(12) United States Patent
Barak

(10) Patent No.: US 11,035,722 B2
(45) Date of Patent: Jun. 15, 2021

(54) METHOD OF READING THE RESULT OF AN ELECTROPHORETIC ASSAY COMPRISING A DIGITAL IMAGE INDICATING THE INTENSITY OF LIGHT EMITTED BY CHEMILUMINESCENCE FROM THE OUTPUT MEDIUM OF THE ELECTROPHORETIC ASSAY

(71) Applicant: Bio-Rad Laboratories, Inc., Hercules, CA (US)

(72) Inventor: Itay Barak, Kibuts Yasur (IL)

(73) Assignee: Bio-Rad Laboratories, Inc., Hercules, CA (US)

( * ) Notice: Subject to any disclaimer, the term of this patent is extended or adjusted under 35 U.S.C. 154(b) by 250 days.

(21) Appl. No.: 16/219,715

(22) Filed: Dec. 13, 2018

(65) Prior Publication Data

US 2019/0186987 A1 Jun. 20, 2019

Related U.S. Application Data

(60) Provisional application No. 62/599,424, filed on Dec. 15, 2017.

(51) Int. Cl.
*G01N 21/76* (2006.01)
*G01J 1/04* (2006.01)
(Continued)

(52) U.S. Cl.
CPC ............ *G01J 1/0403* (2013.01); *G01J 1/0407* (2013.01); *G01N 21/76* (2013.01);
(Continued)

(58) Field of Classification Search
CPC .. G01J 1/0403; G01J 1/0407; G01N 21/6428; G01N 21/76; G01N 33/5302
(Continued)

(56) References Cited

U.S. PATENT DOCUMENTS 3,792,308 A * 2/1974 Ota .................... G02F 1/167
315/150
2008/0240747 A1 10/2008 Ikami
(Continued)

OTHER PUBLICATIONS

International Search Report and Written Opinion in PCT/US2018/065539 dated Feb. 25, 2019; 18 pages.

*Primary Examiner* — Que Tan Le
(74) *Attorney, Agent, or Firm* — Kilpatrick Townsend and Stockton LLP

(57) ABSTRACT

A combination imaging system includes a housing having a base and a lid, the lid having a closed position against the base and having an open position. The imaging device further includes a contact area image sensor. The lid shields the contact area image sensor from ambient light when the lid is in the closed position. The imaging device also includes a camera. The camera includes a lens, and the field of view of the camera encompasses at least a portion of an imaging area of the contact area image sensor when the lid is in the open position. The device may be especially useful for capturing a chemiluminescent image of an electrophoretic assay result, and capturing a colorimetric image of the same result, so that non-chemiluminescent protein standards may be located with respect to chemiluminescent analytes of interest.

11 Claims, 7 Drawing Sheets

(51) Int. Cl.
  *G01N 33/53* (2006.01)
  *G01N 21/64* (2006.01)
(52) U.S. Cl.
  CPC ..... *G01N 33/5302* (2013.01); *G01N 21/6428* (2013.01); *G01N 2021/6439* (2013.01)
(58) Field of Classification Search
  USPC .......................................... 250/208.1, 214 R
  See application file for complete search history.

(56) References Cited

U.S. PATENT DOCUMENTS

| | | |
|---|---|---|
| 2014/0206568 A1 | 7/2014 | Bouzid et al. |
| 2015/0285761 A1 | 10/2015 | Pan et al. |
| 2016/0006910 A1 | 1/2016 | Uri et al. |
| 2016/0161409 A1 | 6/2016 | Ozcan et al. |

\* cited by examiner

METHOD OF READING THE RESULT OF AN ELECTROPHORETIC ASSAY COMPRISING A DIGITAL IMAGE INDICATING THE INTENSITY OF LIGHT EMITTED BY CHEMILUMINESCENCE FROM THE OUTPUT MEDIUM OF THE ELECTROPHORETIC ASSAY

CROSS REFERENCE TO RELATED APPLICATIONS

This application claims the benefit of U.S. Provisional Patent Application No. 62/599,424 filed Dec. 15, 2017 and titled "Combination Imaging of Assays", the entire disclosure of which is hereby incorporated by reference herein for all purposes.

BACKGROUND OF THE INVENTION

Electrophoresis is a technique used in molecular biology and other disciplines to detect the presence of proteins or other analytes in a mixture. Typically, after some preparatory steps, the mixture is placed in "wells" of a gel such as an agarose or polyacrylamide gel. For a protein assay, the gel is subjected to an electric field, which causes the proteins to migrate through the gel. The speed of migration of a particular protein in the mixture through the gel is dependent on the molecular weight of the protein. Proteins having lower molecular weights tend to migrate faster than proteins having higher molecular weights. After a time, the different proteins become separated, since they have traveled different distances through the gel The proteins may be tagged with antibodies such that the proteins of interest emit light by chemiluminescence. In some applications, for example in the well-known Western blotting technique, the proteins are transferred to a membrane such as a polyvinylidene fluoride (PVDF) or nitrocellulose membrane to form a blot. Historically, (after a few incubation steps) the blot was placed in contact with photographic film of about the same size as the blot. The chemiluminescent light exposed portions of the film, so that the pattern of protein separations was permanently recorded on the film. Recently, electronic imaging is replacing photographic film for this purpose.

In any event, one or more "lanes" of the gel are typically reserved for a standard mixture having a set of proteins ("protein standards") of known molecular weight. The standard mixture is separated at the same time as the mixture being assayed, so that the protein standards can provide an indication of how far proteins of given molecular weight have traveled through the gel. This method gives a visual calibration of the assay.

In many assays, the protein standards are visible to the naked eye, but are not chemiluminescent, and thus their locations may not be recorded on the film or using an electronic sensor that records chemiluminescent light. In prior systems, a user might trace the locations of the protein standards on the blot using a chemiluminescent substance, so that the locations of the protein standards can be recorded on film or electronically. Or the user may mark the locations of the protein standards on the film with a standard pen after the film is exposed and developed. Either method is inconvenient.

In another technique known as "gel documentation" or "geldoc", the gel may be imaged directly, without the proteins being transferred to a membrane.

Chemiluminescent protein standards are available, but are much more expensive than protein standards that are not chemiluminescent.

BRIEF SUMMARY OF THE INVENTION

According to one aspect, a combination imaging system comprises a housing having a base and a lid, the lid having a closed position against the base and having an open position. The imaging device further includes a contact area image sensor. The lid shields the contact area image sensor from ambient light when the lid is in the closed position. The imaging device also includes a camera. The camera comprises a lens, and the field of view of the camera encompasses at least a portion of an imaging area of the contact area image sensor when the lid is in the open position. In some embodiments, the camera is mounted in the lid. In some embodiments, the system further comprises a controller configured to capture a first digital image using the contact area image sensor, and capture a second digital image using the camera. In some embodiments, the controller is further configured to combine the first and second digital images into a composite digital image. In some embodiments, the system further comprises a light source controlled by the controller, and the light source provides illumination for the second digital image. The light source may be mounted in the lid. In some embodiments, the system does not include a light source for providing illumination for the second digital image, and the second digital image is captured using ambient light. In some embodiments, the first digital image records the intensity of light emitted by chemiluminescence from a target placed on the contact area image sensor, and the second digital image records the intensity of light reflected from the target. The target may be a blot carrying proteins tagged to emit light by chemiluminescence and also carrying protein standards that are not chemiluminescent. In some embodiments, the system further comprises a lid sensor the senses whether the lid is in the closed position or the open position. In some embodiments, the contact area image sensor is a color sensor. In some embodiments, the camera is a color camera.

According to another aspect, a method of reading the result of an electrophoretic assay comprises placing an output medium of the electrophoretic assay on a contact area image sensor of a combination imaging device, and closing a lid of the combination imaging device, blocking ambient light from reaching the contact area image sensor. The method further comprises capturing a first digital image of the output medium using the contact area image sensor. The first digital image indicates the intensity of light emitted by chemiluminescence from the output medium. The method further comprises opening the lid, and capturing a second digital image of the output medium using a camera mounted in the lid. The field of view of the camera encompasses at least a portion of the output medium when the lid is in an open position, and the second digital image indicates the intensity of light reflecting from the output medium. The first and second digital images are combined into a composite digital image. In some embodiments, the output medium is a blot, the blot carrying proteins tagged to emit light by chemiluminescence and the carrying protein standards that are not chemiluminescent but are visible the second digital image; and combining the first and second digital images into a composite digital images comprises combining the first and second digital images into a digital image in which both the chemiluminescence from the tagged proteins and the non-chemiluminescent protein standards are shown. In some embodiments, the first digital image is captured before the second digital image is captured, or the second digital image is captured before the first digital image is captured. In some embodiments, the output medium is a membrane. In some embodiments, the combination imaging device does not include a light source for providing illumination for the second digital image, and capturing the second digital image comprises capturing the second digital image using ambient light. In some embodiments, the method further comprises providing supplemental light to the output medium using a light source in the combination imaging device, and capturing the second digital image comprises capturing the second digital image using the supplemental light. In some embodiments the method further comprises digitally adjusting the size of at least one of the first and second digital images so that the first and second digital images are of the same size. In some embodiments, the method further comprises digitally removing distortion from at least one of the first and second digital images. In some embodiments, the method further comprises sensing whether the lid is in the closed position or an open position, and instructing a user of the imaging device to open or close the lid. In some embodiments, the method further comprises placing a gel on the contact area image sensor, and capturing one or more images of the gel using the contact area image sensor, the camera, or both.

According to another aspect, a combination imaging system comprises a housing having a base and a lid, the lid having a closed position against the base and having an open position, and a contact area image sensor. The lid shields the contact area image sensor from ambient light when the lid is in the closed position. The system further comprises a phosphorescent area in the lid corresponding to the area of the contact area image sensor when the lid is in the closed position, and a shutter for covering the phosphorescent area.

According to another aspect, a method of reading the result of an electrophoretic assay comprises placing an output medium of the electrophoretic assay on a contact area image sensor of a combination imaging device, covering a phosphorescent area in the lid of the combination image device, and capturing a first digital image of the output medium using the contact area image sensor. The first digital image indicates the intensity of light emitted by chemiluminescence from the output medium, and the first digital image is captured with the lid of the combination imaging device closed, blocking ambient light from reaching the contact area image sensor. The method further comprises uncovering the phosphorescent area in the lid of the combination imaging device, and capturing a second digital image of the output medium using the contact area image sensor. The second digital image indicates the intensity of light passing through the output medium from the phosphorescent area, and the second digital image is captured with the lid of the combination imaging device closed, blocking ambient light from reaching the contact area image sensor. The method further comprises combining the first and second digital images into a composite digital image.

DETAILED DESCRIPTION OF THE INVENTION

Figure 1:
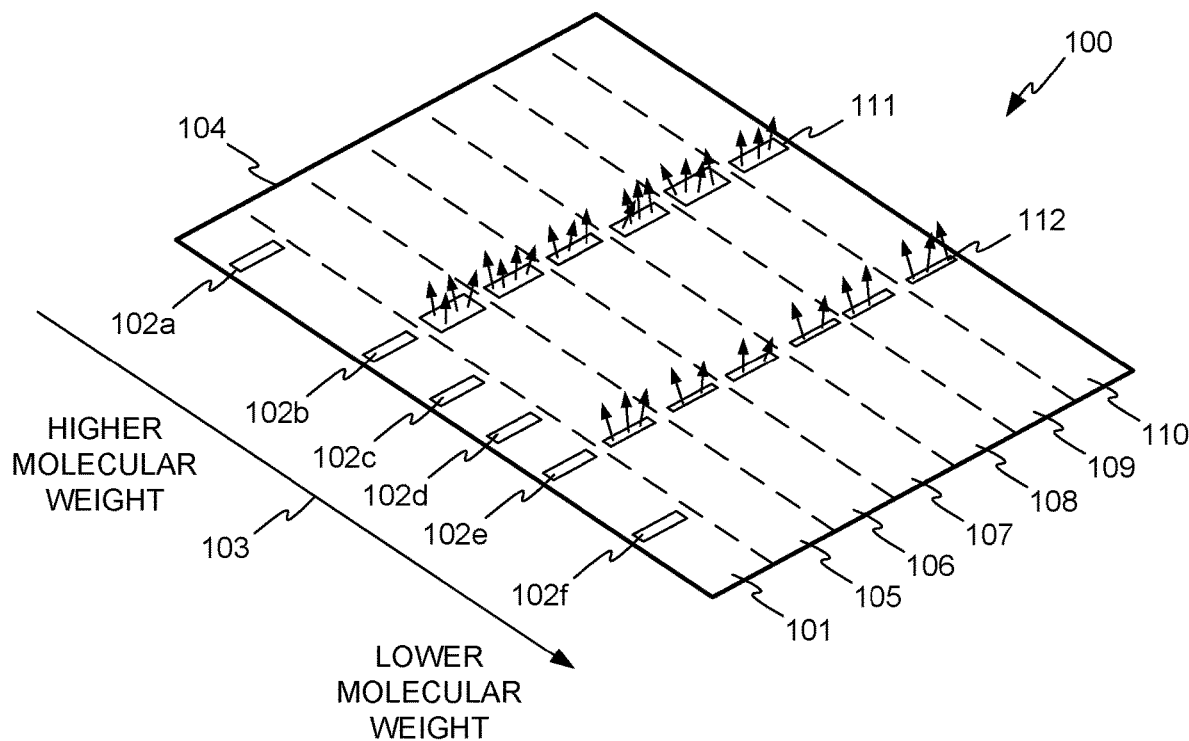
FIG. 1 illustrates a typical blot after separation of proteins and the several incubation steps, in accordance with embodiments of the invention.

FIG. 1 illustrates a typical blot 100 after separation of proteins, in accordance with embodiments of the invention. One lane 101 of the blot is reserved for protein standards 102*a*-102*f*. Protein standards 102*a*-102*f* have been separated in direction 103, with lower molecular weight protein standard 102*f* being farther from edge 104 than higher molecular weight protein standard 102*a*.

Samples of the mixture to be assayed have been separated in lanes 105-110, resulting in protein bands 111 and 112 in each of lanes 105-110. (The lane divisions shown in dashed lines are for illustration only, and do not appear on a blot.) Protein band 111 corresponds approximately to the molecular weight of protein standard 102*b*, and protein band 112 corresponds approximately to the molecular weight of protein standard 102*e*. Because standards 102*b* and 102*e* are of known weight, their presence provides information about the molecular weights of the proteins at bands 111 and 112, to assist in identifying the proteins in bands 111 and 112.

As is indicated in FIG. 1, the proteins in bands 111 and 112 are emitting light via chemiluminescence, while protein standards 102*a*-102*f* are not emitting light.

Figure 2:
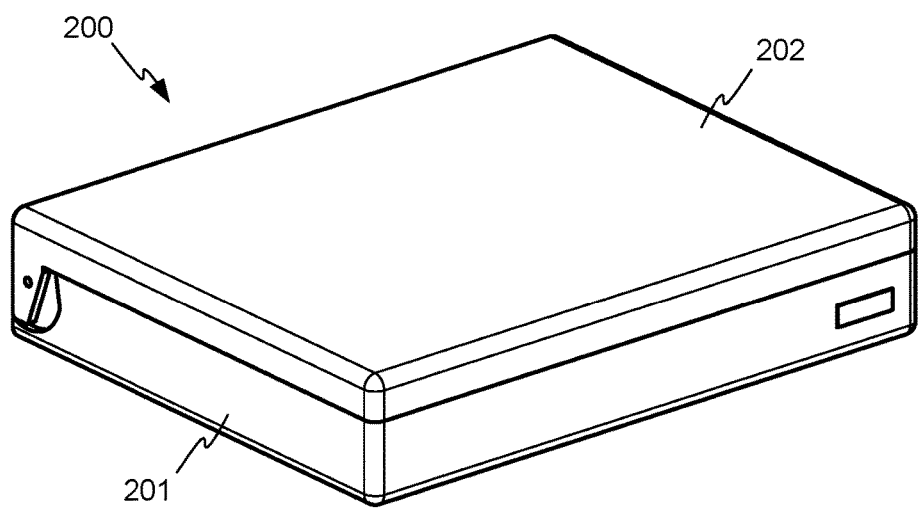
FIG. 2 illustrates an imaging device in accordance with embodiments of the invention, in a closed position.
Figure 3:
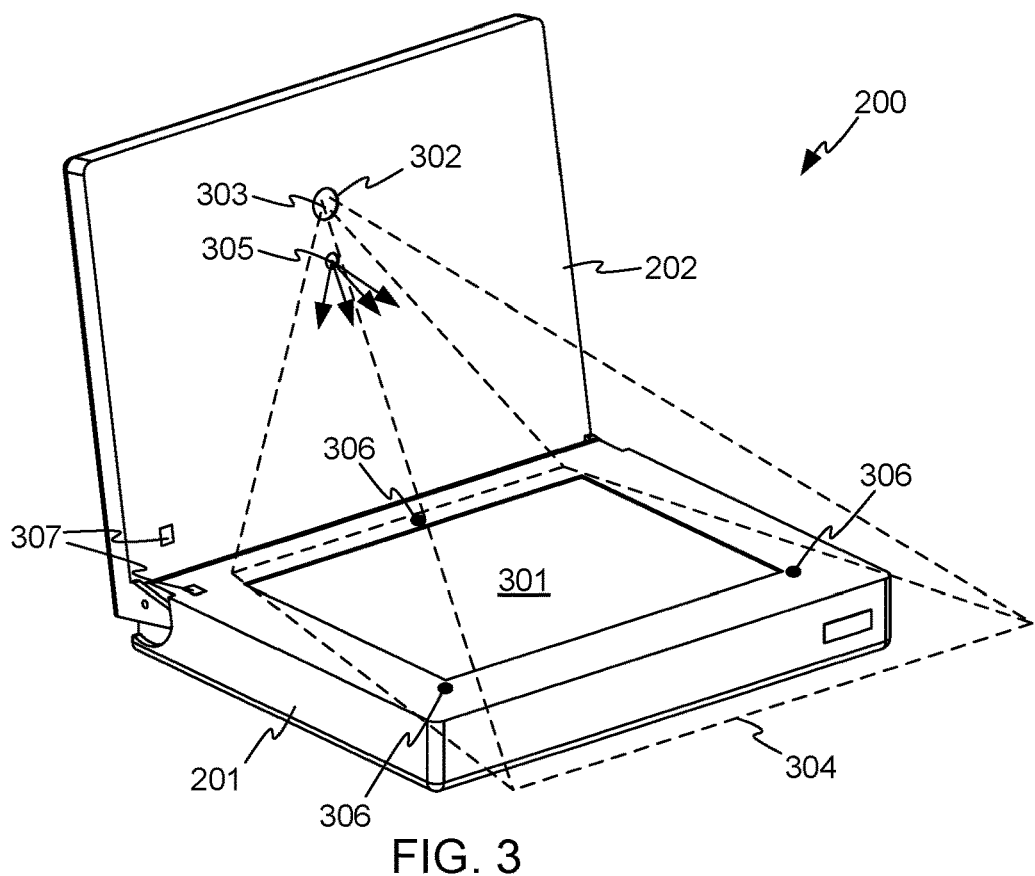
FIG. 3 shows the imaging device of FIG. 2 in an open position.

FIG. 2 illustrates an imaging device 200 in accordance with embodiments of the invention, in a closed position. FIG. 3 shows imaging device 200 in an open position.

Referring to both FIG. 2 and FIG. 3, imaging device 200 includes a base portion 201 and a lid 202. Lid 202 is shown in a closed position in FIG. 2, and in an open position in FIG. 3. A contact area image sensor 301 is disposed in base 201. Contact area image sensor 301 may be, for example, of the kind described in U.S. Patent Application Publication No. 2015/0172526 of Swihart et al., published Jun. 18, 2015 and titled "Non-Destructive Read Operations with Dynamically Growing Images"; U.S. Patent Application Publication No. 2016/0006910 of Uri et al., published Jan. 7, 2016 and titled "Contact Imager"; U.S. Patent Application Publication No. 2016/0028976 of Ran et al., published Jan. 28, 2016 and titled "Digital Imaging with Masked Pixels", U.S. Patent Application Publication No. 2017/0016829 of Swihart et al., published Jan. 19, 2017 and titled "Contact Imaging Devices for Fluorescence Applications"; the entire disclosures of which are hereby incorporated by reference herein for all purposes.

Contact area image sensor 301 may be, for example a charge coupled device (CCD) sensor, a complementary metal oxide semiconductor (CMOS) sensor, or another suitable kind of sensor. In general, such sensors exploit the property of some semiconductor materials that when the material is struck by light, free electrons are generated in proportion to the intensity of the light. The sensor is divided into specific light-sensitive areas called "pixels". To capture an image, the pixels are reset and then exposed to light for an exposure time. At the end of the exposure time, the amount of charge accumulated in each pixel is measured and converted to a numerical value. An array of these numerical values may be called a "digital image", with each value in the array representing the brightness of the light falling on the corresponding pixel.

In a CCD sensor, the accumulated charges are shifted off of the sensor to a charge amplifier, the output of which is digitized for each pixel. In a CMOS sensor, the accumulated charge can be read from each pixel directly, without shifting. In some sensors, different pixels are sensitive to different light wavelength bands, enabling color imaging.

In this context, a "contact" sensor is one that receives light directly from locations on the target in contact with a face of the sensor, with 1:1 magnification and without any intervening magnification-changing optics. (There may be other kinds of optical components between the contact surface and the light-sensitive semiconductor layer, as is explained in more detail below.) This kind of sensing is analogous to the making of a "contact print" in film photography, in which a photographic negative is placed in direct contact with photo paper and exposed to light. An image is formed on the paper that is the exact size of the negative.

Referring again to FIG. 3, contact area image sensor 301 is preferably slightly larger in area than a typical blot, for example about 7×10 centimeters. In other embodiments, contact area image sensor 301 may be about 5×7 inches, 8×10 inches, or 9×12 inches, or another suitable size. Contact area image sensor 301 preferably includes many thousands or even millions of pixels, which are small enough that a digital image captured by contact area image sensor 301 provides a high resolution representation of a target placed on the sensor. For example, each pixel may be about 130 microns square, or another suitable size. A sensor 7×10 centimeters with 130-micron pixels would have about 414,000 total pixels.

Imaging device 200 also includes a camera 302 mounted in lid 202. Camera 302 preferably includes lens 303 and another electronic image sensor (not visible in FIGS. 2 and 3). Lens 303 has a field of view 304, which encompasses at least part of and preferably all of contact area image sensor 301 when lid 202 is in the open position of FIG. 3. Field of view 304 is the region visible to the sensor in camera 302 through lens 303. Imaging device 200 preferably includes a mechanism for indicating when lid 202 is in a particular open position, for example a rotary stop, a detent, or another mechanism. Camera 302 may be designed in concert with base 201, lid 202, and contact area image sensor 301 to ensure that the field of view of camera 302 encompasses some or all of contact area image sensor 301 when lid 202 is in the open position.

Imaging device 200 may optionally include a light source 305, which may include, for example, one or more light emitting diodes (LEDs) or other suitable light emitting devices. The light emitted by light source 305 may be broadband light, white light, narrow band light, monochromatic light, or may have another suitable wavelength distribution.

Optionally, one or more fiducial markings 306 may be placed on base 201 within field of view 304 of camera 302. A lid sensor 307 may be present, allowing automatic detection of whether lid 202 is in its closed or open position.

While FIG. 3 shows camera 302 and light source 305 mounted in lid 202, this is not a requirement, Either or both of these components could be mounted differently, for example suspended over contact area image sensor 301 by some other structure.

Camera 302 can photograph a target on contact area image sensor 301 from above, by capturing light reflected from the target and forming an image of the target on the sensor within camera 302. An image taken with reflected light may be called a "colorimetric" image, as compared with "chemiluminescent" image taken using contact area image sensor 301 using only light emitted by the target by chemiluminescence. The reflected light may come from ambient room light, or may be supplied by light source 305, or may be a combination of ambient and artificial light. Using light source 305 may be preferable, so that the quality and uniformity of the image captured by camera 302 is not so subject to variations in ambient room light. Light source 305 may be designed in concert with base 201, lid 202, and contact area image sensor 301 so that the area of contact area image sensor 301 is illuminated by light source 305 when lid 202 is in the open position.

Figure 4:
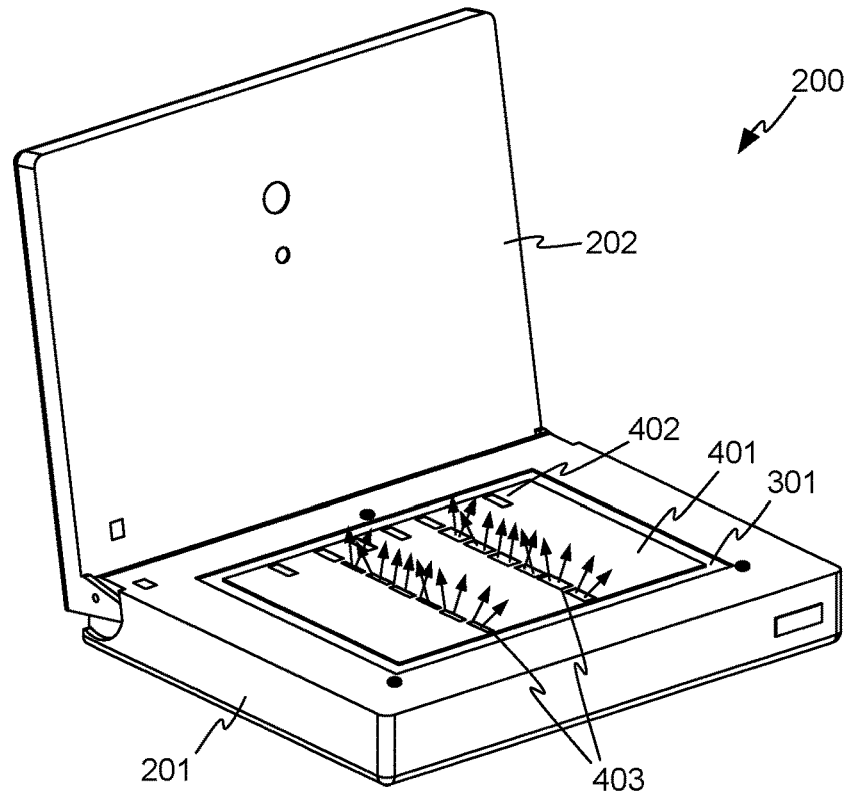
FIG. 4 shows the imaging device of FIG. 2 with a target in place, in accordance with embodiments of the invention.

FIGS. 4-8 illustrate steps in the use of imaging device 200. In FIG. 4, lid 202 has been opened, and a target 401 in the form of a blot similar to blot 100 is placed on contact area image sensor 301. Target 401 includes a lane 402 of protein standards that do not emit light, as well as a number of locations 403 that do emit light by chemiluminescence, indicating the presence of particular proteins that have been separated in the experiment. While only the top surface of target 401 is visible in FIG. 4, the chemiluminescent light is emitted from both sides, and some of the light is directed downward toward contact area image sensor 301.

Figure 5:
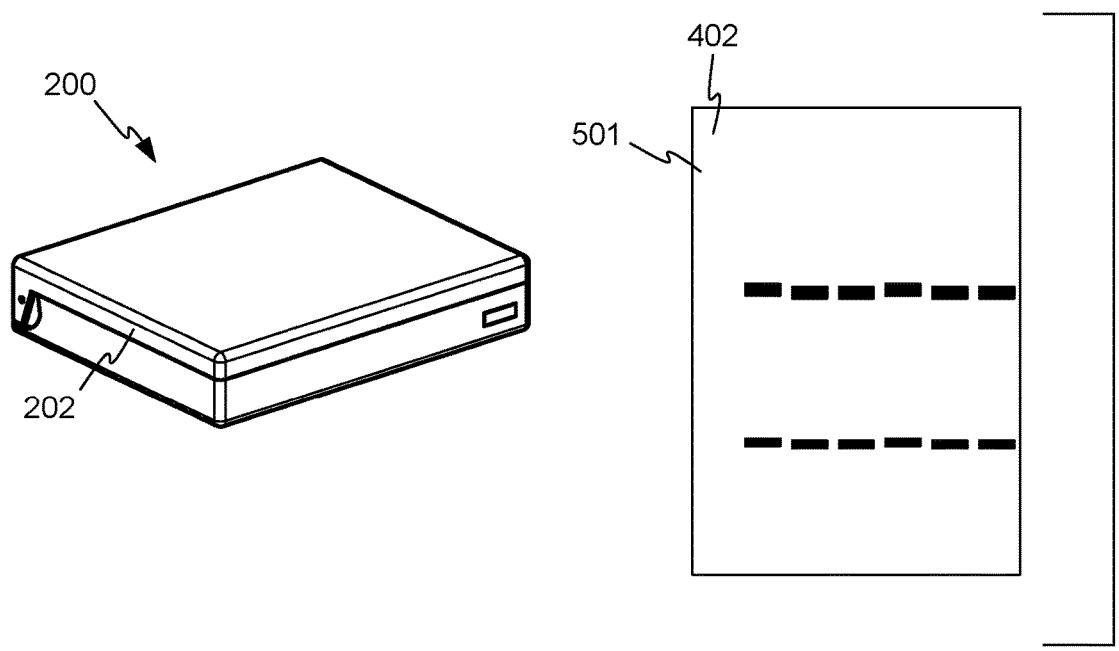
FIG. 5 shows the imaging device of FIG. 2 in a closed position, and an example chemiluminescent digital image, in accordance with embodiments of the invention.

Once target 401 is in place, lid 202 is closed, as shown in FIG. 5. Lid 202 shields contact area image sensor 301 from ambient light when lid 202 is in the closed position. With lid 202 in the closed position, a digital image 501 is captured using contact area image sensor 301.

The generation of digital image 501 from the output of contact area image sensor 301 may be accomplished in any suitable way. For example, imaging device 200 may contain a controller that performs all of the necessary conversions and calculations, and stores digital image 501 in a standard image file format such as JPEG (Joint Photographic Experts Group), TIFF (Tagged Image File Format), GIF (Graphics Interchange Format), PNG (Portable Network Graphics), or any other suitable standardized or proprietary format. In other embodiments, signals may be passed from imaging device 200 to a suitable computer system, which converts the signals and generates the digital image file. Any workable architecture and division of tasks may be used.

Digital image 501 adopts the convention that background areas (where no chemiluminescent light was detected) are shown in white, while areas where chemiluminescent light was detected (corresponding to proteins of interest) are shown in black. The reverse convention could be adopted, or the areas could be distinguished in any other suitable way, for example using gray levels, colors, false colors, or another distinguishing technique.

Notably, let leftmost portion of digital image 501, corresponding to protein standards lane 402 of target 401, does not indicate the detection of any light. This is because the protein standards are not chemiluminescent and do not generate light.

It will be recognized that the above description of image capture using contact area array sensor 301 is somewhat simplified. Other techniques may be utilized to improve the quality of chemiluminescent images, for example compensation for dark current and temperature variation across contact area array sensor 301, as described in U.S. Patent Application Publication No. 20126/0028976 of Ran et al., and nondestructive reading of intermediate images to assist in determining when to end an exposure and reducing noise, as discussed in U.S. Patent Application Publication No. 2015/0172526 of Swihart et al., both of which were previously incorporated herein by reference.

Figure 6:
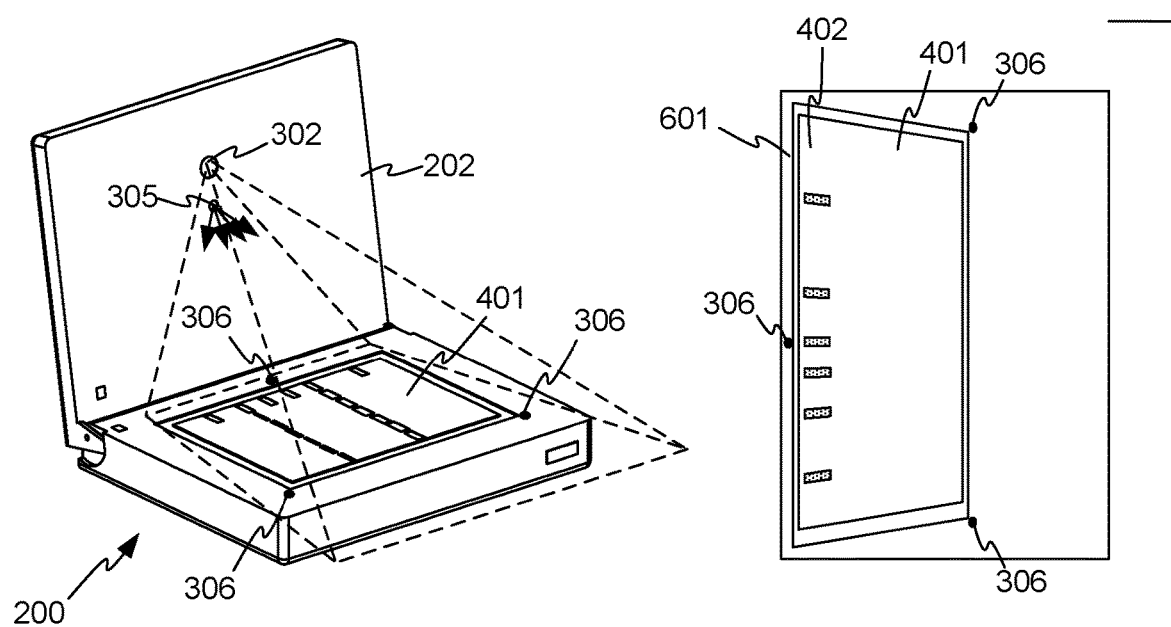
FIG. 6 shows the imaging device of FIG. 2 in an open position, and an example colorimetric digital image, in accordance with embodiments of the invention.

FIG. 6 shows imaging device 200 with lid 202 again in the open position. In this position, another digital image 601 is captured using camera 302, either by ambient light or using light emitted from a light source such as light source 305, or using a combination of light sources. Because of the oblique angle at which camera 302 views contact area image sensor 301, target 401 appears with perspective distortion image 601. However, because the physical relationship of camera 302 to target 401 is known, the perspective distortion can be undone digitally through straightforward image processing. In addition, if fiducial marks are used, they can appear in image 601 and provide additional cues for digitally reversing the perspective distortion. Also in image 601, the protein standards are visible in lane 402.

Figure 7:
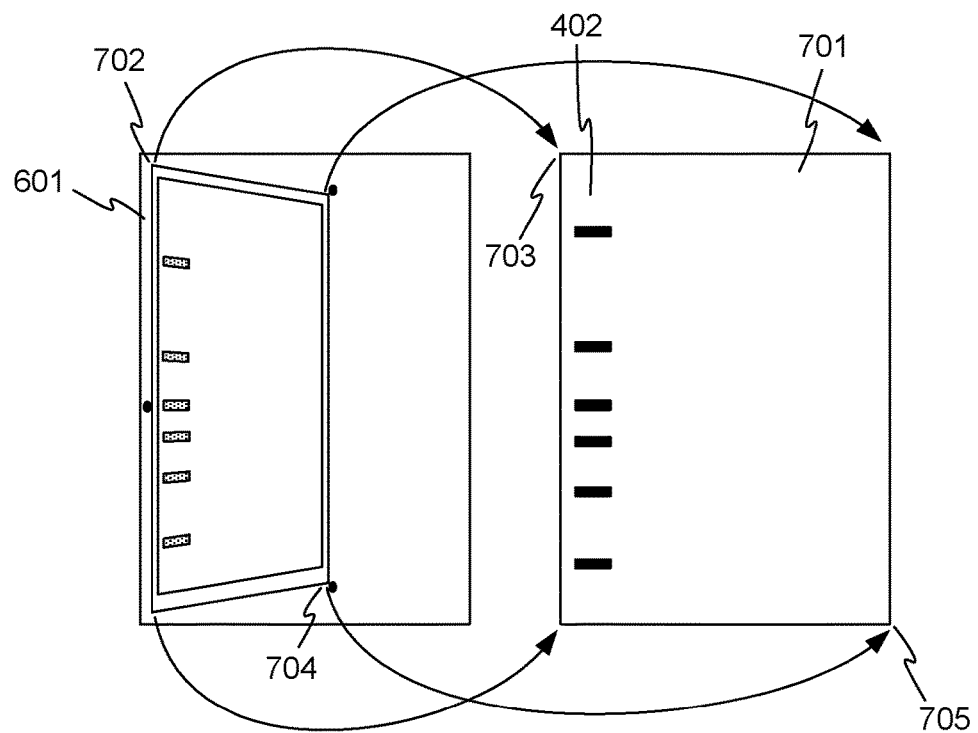
FIG. 7 shows the transformation of a digital image into a corrected image with perspective distortion removed, in accordance with embodiments of the invention.

FIG. 7 shows the transformation of uncorrected image 601 into a corrected camera image 701, with the perspective distortion removed. In addition, image 701 is preferably scaled to have the same or nearly the same pixel dimensions as image 501 taken using contact area image sensor 301. In this example, pixel 702 in image 601 has been mapped to pixel 703 in image 701. Similarly, pixel 704 in image 601 has been mapped to pixel 705 in image 701. Other pixels in image 601 are mapped to corresponding pixels in image 701 based on their positional relationships to pixels 702 and 704. It may be preferable that the sensor in camera 302 have significantly more pixels than contact area array sensor 301, so that the perspective distortion correction does not introduce objectionable "jaggies" or other noticeable image artifacts.

Other image transformations may be performed as well, for example smoothing of the brightness of the image to compensate for non-uniformity of the illumination used to capture image 601, contrast enhancements, and the like. The net result is that image 701 is the same size as image 501, and shows the protein standards in lane 402. However, the proteins of interest in the other lanes may not be visible in digital image 701, because the chemiluminescent light emission is weak in relation to the ambient or artificial light used to capture colorimetric image 601.

In other embodiments, for example if camera 302 is suspended over contact area image sensor 301 using a fixed structure rather than being mounted in lid 202, the image processing may be simplified because camera 302 may be able to capture images without perspective distortion.

Figure 8:
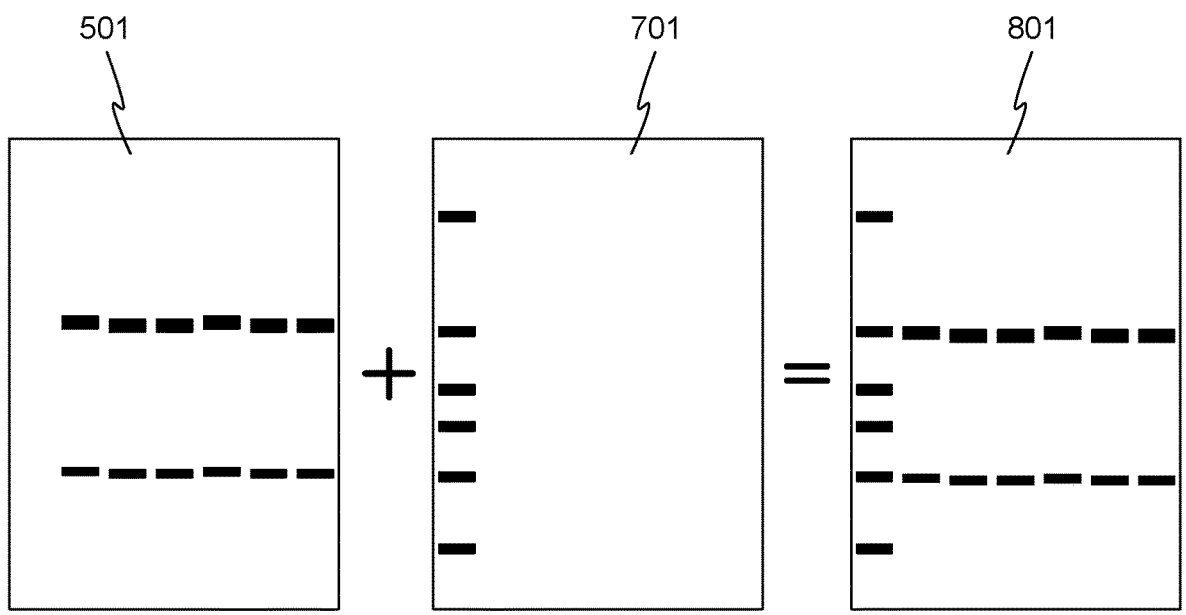
FIG. 8 illustrates the construction of a composite digital image, in accordance with embodiments of the invention.

Finally, as shown in FIG. 8, digital image 501 (captured in chemiluminescent light using contact area array sensor 301) and digital image 701 (captured colorimetrically using camera 302) are combined into a composite digital image 801. For example, if the digital images use the convention that darker areas represent protein standards or proteins of interest, digital image 801 may be constructed by selecting for each pixel the darker of the corresponding pixels in images 501 and 701.

While the examples above are described in the context of reading a blot such as a Western blot, embodiments of the invention may be used for direct gel documentation as well. In gel documentation, the electrophoretic gel is read directly, without the step of transferring the separated proteins and protein standards to a membrane. The gel itself can be placed on contact area image sensor 301, and imaged colorimetrically, using ambient light, light from light source 305, or a combination of the two. In either event, the membrane or the gel may be considered to be an output medium of an electrophoretic assay, since the membrane or gel indicates the results of the assay. A gel may also be imaged using camera 302, in addition to or instead of contact area image sensor 301.

Figure 9:
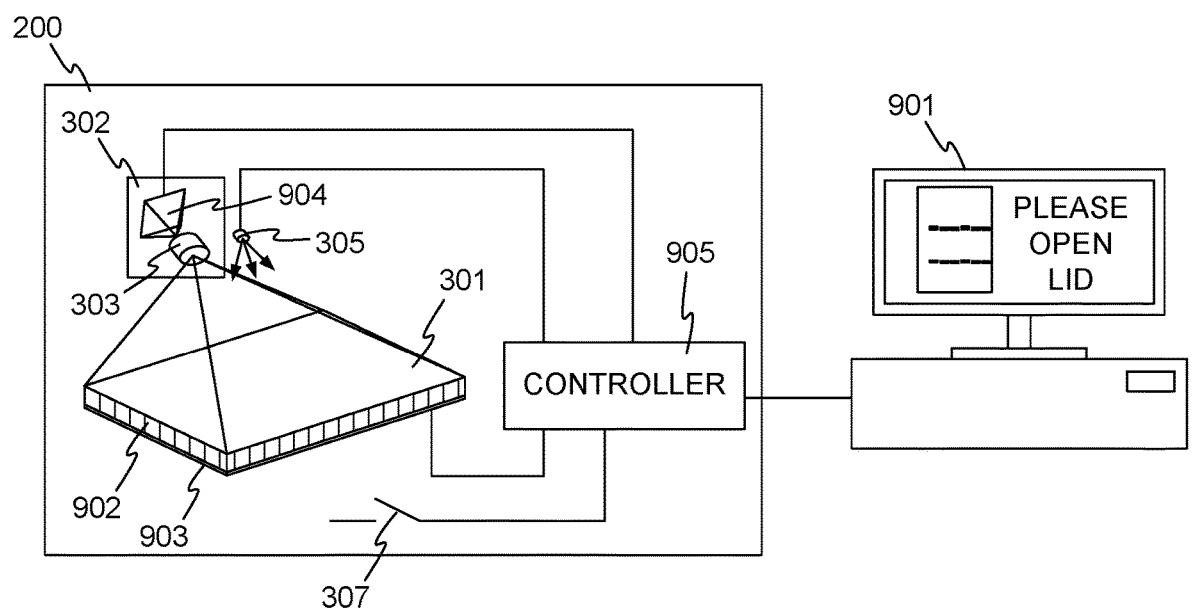
FIG. 9 illustrates a schematic block diagram of the imaging device of FIG. 2, in accordance with embodiments of the invention, and a computer system connected to the imaging device.

FIG. 9 illustrates a schematic diagram of imaging device 200, in accordance with embodiments of the invention, and a computer system 901 connected to imaging device 200.

Imaging device 200 includes contact area image sensor 301, some aspects of which are described above. More details are visible in FIG. 9. For example, contact area image sensor 301 may include a faceplate layer 902 atop a light-sensitive semiconductor layer 903. Faceplate layer may include a bundle of parallel optical fibers arranged with their axes vertical. The fibers may be gradient index lenses or simple optical fibers. Faceplate layer 902 has the effect of transferring light entering at the top of the fibers to the bottom ends of the fibers, so that an image formed at the tops of the fibers is translated downward to the bottom ends of the fibers. The bottom side of faceplate layer 902 is in substantial contact with light-sensitive semiconductor layer 903. This arrangement may provide protection for light-sensitive semiconductor layer 903 and its associated circuitry, and allows forming of an image on light-sensitive semiconductor layer 903 without the use of other optics such as magnification-changing lenses or the like. The top of faceplate layer 902 forms the platen of the imaging device, on which targets are placed directly.

Camera 302 forms its images differently. In camera 302, lens 303 projects an image of the platen onto an electronic array light sensor 904. Electronic array light sensor 904 may be, for example, a CMOS sensor, a CCD sensor, or another kind of sensor. Electronic array light sensor 904 also includes thousands or millions of pixels, but the pixels in electronic array light sensor 904 are preferably much smaller than the pixels of contact area image sensor 301. For example, electronic array light sensor 904 may include as few as 200,000 pixels or as many as several million pixels, or another suitable number. Each pixel may be about 1 to 6 microns across, or another suitable dimension. Electronic array light sensor 904 may be a color sensor, meaning that different pixels are sensitive to different light wavelengths, enabling camera 302 to distinguish color.

A controller 905 is coupled to the various components of imaging device 200, including contact area image sensor 301, light source 305, lid sensor 307, and electronic array light sensor 904. Controller 905 is coupled to computer system 901 by any suitable interface, for example a Universal Serial Bus (USB) interface or another kind of interface. Computer system 901 may provide instructions to imaging device 200 as to when to capture chemiluminescent and colorimetric mages and the like, and may provide a user interface to accept instructions from user of the system, and to present results to the user. Computer system 901 may cooperate with imaging device 200 to provide image processing for exposure determination, distortion correction, or other functions. Computer system 901 preferably includes a processor and a stored program that, when executed by the processor, causes computer system 901 to perform its prescribed functions.

In other embodiments, image processing and the like may be performed by controller 905, within imaging device 200. Any suitable division of labor between imaging device 200 and computer system 901 may be used. In other embodiments, imaging device 200 may be a standalone system, including a user interface and display, so that assays can be read without the need of an external computer system. In that case, results may be stored on removable storage media for transfer to other devices, or imaging device 200 may include a network interface for sending results to a remote server. The network interface may be used for other functions as well, for example downloading software updates and other functions.

Figure 10:
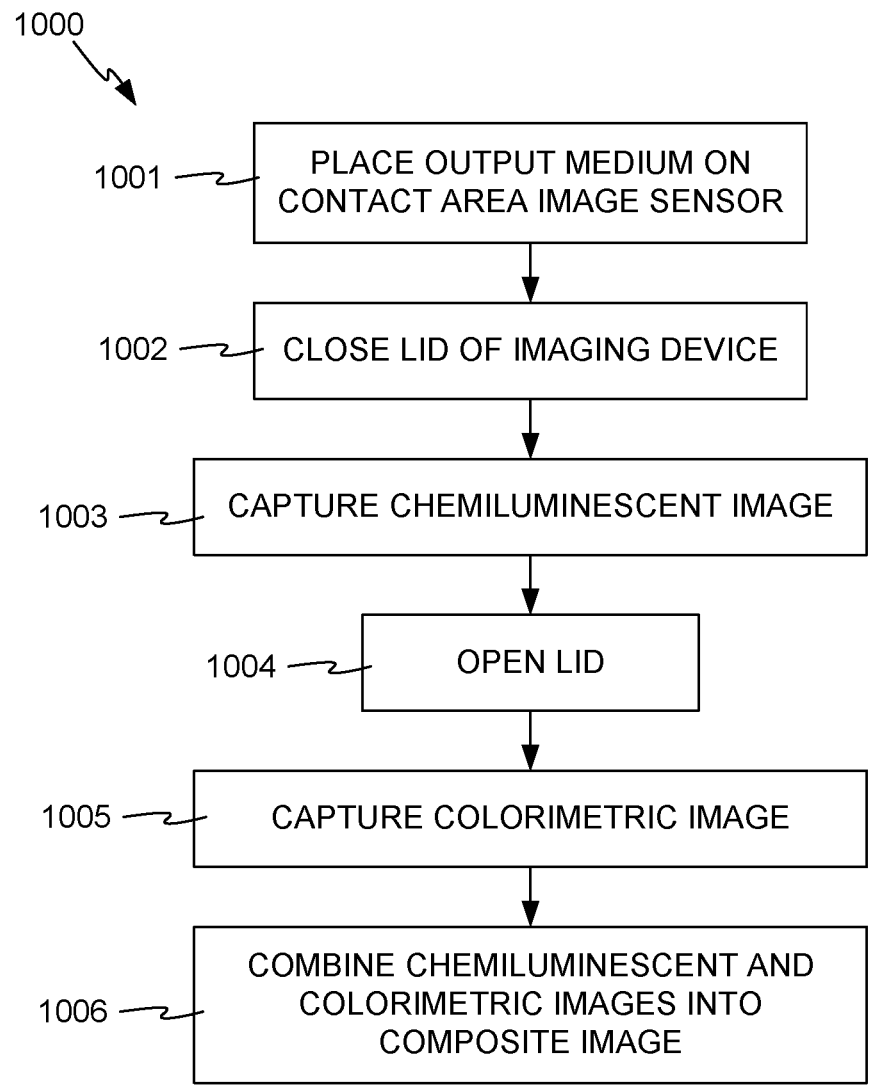
FIG. 10 shows a flow chart of a method in accordance with embodiments of the invention.

FIG. 10 illustrates a flow chart of a method 1000 in accordance with embodiments of the invention. In step 1001, an output medium of an electrophoretic assay is placed on a contact area image sensor of an imaging device. For example, the output medium may be a membrane onto which proteins have been transferred.

At step 1002, a lid of the imaging device is closed, blocking ambient light from reaching the contact area image sensor. At step 1003, a first digital image of the output medium is captured, using the contact area image sensor. The first digital image indicates the intensity of light emitted by chemiluminescence from the output medium, and may be termed a "chemiluminescent" image.

At step 1004, the lid is opened. At step 1005, a second digital image is captured using a camera, which may be mounted in the lid. The field of view of the camera encompasses at least a portion of the output medium when the lid is in an open position. The second digital image indicates the intensity of light reflecting from the output medium.

In step 1006, the first and second digital images are combined into a composite digital image. While the examples above have described the chemiluminescent image being captured before the colorimetric image, this is not a requirement. The images may be captured in any order. The terms "first digital image" and "second digital image" as used herein are to distinguish the two digital images, and do not convey any temporal relationship.

Figure 11:
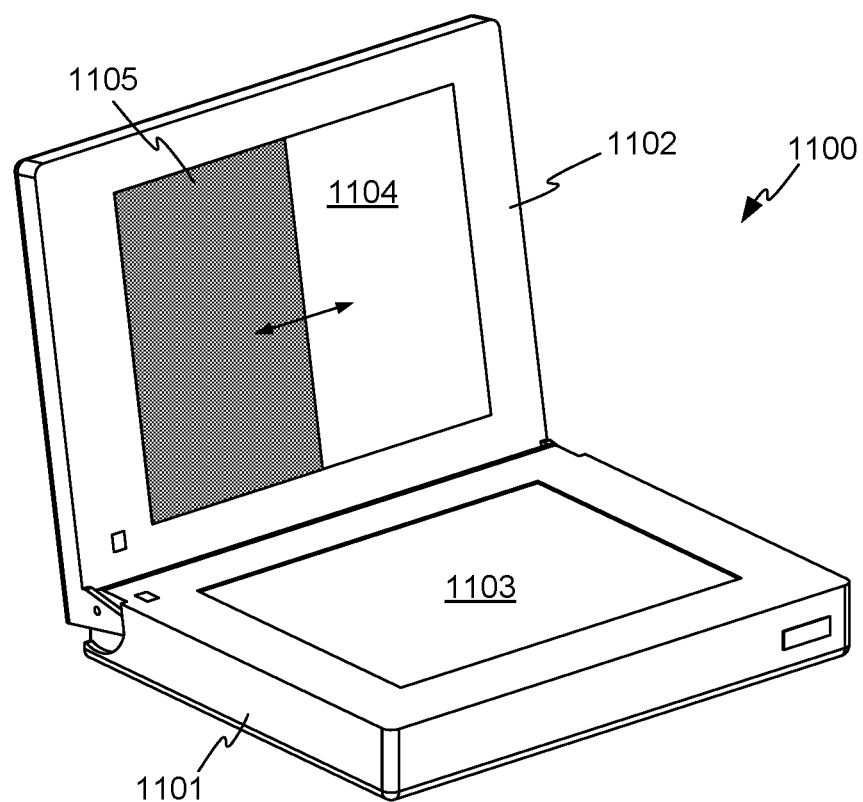
FIG. 11 illustrates an imaging device in accordance with other embodiments of the invention, in an open position.

FIG. 11 illustrates a combination imaging device 1100, in accordance with other embodiments of the invention. Combination imaging device 1100 includes a base 1101, a lid 1102, and a contact area image sensor 1103, similar to those described above with respect to other embodiments.

Combination imaging device 1100 further comprises a phosphorescent area 1104 in lid 1102. Phosphorescent area 1104 corresponds to the area of contact area image sensor 1103 when lid 1102 is closed. Phosphorescent area 1104 may be, for example, a sheet of phosphorescent material embedded in lid 1102. A shutter 1105 is moveable to cover or uncover phosphorescent area 1104. Shutter 1105 may be a mechanical shutter as shown, or may be an electronic shutter or another kind of shutter. When shutter 1105 is closed, phosphorescent area 1104 can act as a backlight for contact area image sensor 1103, enabling combination electroluminescent and colorimetric imaging.

To read the result of an electrophoretic assay using combination imaging device 1100, the user ensures that phosphorescent area 1104 is exposed to light for a sufficient amount of time to "charge" it with light, so that phosphorescent area 1104 is self-luminescent for a time. The user then places the output medium of the assay, for example a blot, on contact area image sensor 1103 and closes lid 1102. Phosphorescent area 1104 produces light to backlight the output medium. A first image is captured using contact area image sensor 1103. Any protein standards in the output medium are visible in the image.

The user then closes shutter 1105, blocking light from phosphorescent area 1104 from reaching contact area image sensor 1103. With lid 1102 closed, a second image is captured using contact area image sensor 1103, of the light emitted from the output medium via chemiluminescence. The chemiluminescent analytes of interest will be visible in this second image. The first and second images can be combined into a composite image showing both the protein standards and the analytes of interest.

While the process is described above with the phosphorescence image captured first, the images can be captured in any order. The order may be selected based on the expected exposure times of the two images, the amount of time that phosphorescent area 1104 can emit sufficient light, and the amount of time that the chemiluminescence reactions at the analytes of interest will be sufficiently bright for robust detection.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. The invention has now been described in detail for the purposes of clarity and understanding. However, those skilled in the art will appreciate that certain changes and modifications may be practiced within the scope of the appended claims.

What is claimed is:

1. A method of reading the result of an electrophoretic assay, the method comprising:
    placing an output medium of the electrophoretic assay on a contact area image sensor of a combination imaging device;
    closing a lid of the combination imaging device, blocking ambient light from reaching the contact area image sensor;
    capturing a first digital image of the output medium using the contact area image sensor, the first digital image indicating the intensity of light emitted by chemiluminescence from the output medium;
    opening the lid;
    capturing a second digital image of the output medium using a camera mounted in the lid, the field of view of the camera encompassing at least a portion of the output medium when the lid is in an open position, wherein the second digital image indicates the intensity of light reflecting from the output medium; and
    combining the first and second digital images into a composite digital image.

2. The method of claim 1, wherein:
    the output medium is a blot, the blot carrying proteins tagged to emit light by chemiluminescence and the blot carrying protein standards that are not chemiluminescent but are visible the second digital image; and
    combining the first and second digital images into a composite digital image comprises combining the first and second digital images into a digital image in which both the chemiluminescence from the tagged proteins and the non-chemiluminescent protein standards are shown.

3. The method of claim 1, wherein:
the first digital image is captured before the second digital image is captured; or
the second digital image is captured before the first digital image is captured.

4. The method of claim 1, wherein the output medium is a membrane.

5. The method of claim 1, wherein the combination imaging device does not include a light source for providing illumination for the second digital image, and wherein capturing the second digital image comprises capturing the second digital image using ambient light.

6. The method of claim 1, further comprising providing supplemental light to the output medium using a light source in the combination imaging device, wherein capturing the second digital image comprises capturing the second digital image using the supplemental light.

7. The method of claim 1, further comprising digitally adjusting the size of at least one of the first and second digital images so that the first and second digital images are of the same size.

8. The method of claim 1, further comprising digitally removing distortion from at least one of the first and second digital images.

9. The method of claim 1, further comprising:
sensing whether the lid is in the closed position or an open position; and
instructing a user of the imaging device to open or close the lid.

10. The method of claim 1, further comprising:
placing a gel on the contact area image sensor; and
capturing one or more images of the gel using the contact area image sensor, the camera, or both.

11. A method of reading the result of an electrophoretic assay, the method comprising:
placing an output medium of the electrophoretic assay on a contact area image sensor of a combination imaging device;
covering a phosphorescent area in the lid of the combination image device;
capturing a first digital image of the output medium using the contact area image sensor, the first digital image indicating the intensity of light emitted by chemiluminescence from the output medium, wherein the first digital image is captured with the lid of the combination imaging device closed, blocking ambient light from reaching the contact area image sensor;
uncovering the phosphorescent area in the lid of the combination imaging device;
capturing a second digital image of the output medium using the contact area image sensor, wherein the second digital image indicates the intensity of light passing through the output medium from the phosphorescent area, wherein the second digital image is captured with the lid of the combination imaging device closed, blocking ambient light from reaching the contact area image sensor; and
combining the first and second digital images into a composite digital image.

* * * * *